United States Patent [19]

Blitshteyn et al.

[11] Patent Number: 5,137,352
[45] Date of Patent: Aug. 11, 1992

[54] METHOD AND APPARATUS FOR DETERMINING THE CONTACT ANGLE OF LIQUID DROPLETS ON CURVED SUBSTRATE SURFACES

[75] Inventors: Mark Blitshteyn, Bloomingdale; Joergen Hansen, Schaumburg; Robert K. Shaw, Wildwood, all of Ill.

[73] Assignee: Tantec, Inc., Schaumburg, Ill.

[21] Appl. No.: 650,675

[22] Filed: Feb. 5, 1991

[51] Int. Cl.$^5$ .................. G01B 11/26; G01N 13/02
[52] U.S. Cl. ............................. 356/138; 73/64.52
[58] Field of Search ................... 356/138; 73/64.4

[56] References Cited

U.S. PATENT DOCUMENTS 4,688,938 8/1987 Demoulin et al. ................ 356/138

OTHER PUBLICATIONS

Mclachlan et al., "Apparatus for Measuring the Contact Angles at Crystal Solution Vapor Interfaces", Rev. Sci. Instrum. vol. 46, #1, Jan. 1975.
Wagner, "Spreading of Liquid Drops on Cylindrical Surfaces: Accurate Determination of Contact Angle", J. Appl. Phys., vol. 67, #3, Feb. 1, 1990.

Primary Examiner—F. L. Evans
Assistant Examiner—K. P. Hantis
Attorney, Agent, or Firm—Leydig, Voit & Mayer

[57] ABSTRACT

A method and apparatus adapted for the rapid, accurate and repeatable determination of contact angles of liquid droplets applied to curved substrate surfaces. The apparatus includes a support upon which an article may be mounted with the curved substrate surface facing downwardly, a pipette having a discharge end below the downwardly facing curved surface and operable for transferring a predetermined relatively small droplet of a test liquid onto the downwardly facing curved surface, and a contact angle measuring device which includes a lamp for directing a light beam across the suspended droplet such that an image thereof is projected onto a screen from which the contact angle is measurable.

29 Claims, 4 Drawing Sheets

METHOD AND APPARATUS FOR DETERMINING THE CONTACT ANGLE OF LIQUID DROPLETS ON CURVED SUBSTRATE SURFACES

FIELD OF THE INVENTION

The present invention relates generally to a method and apparatus for determining the contact angle between a liquid droplet and a substrate surface upon which it is deposited, and more particularly, to a method and apparatus for determining the contact angle between a liquid droplet and convex or otherwise curved substrate surfaces.

BACKGROUND OF THE INVENTION

Contact angle measurements of liquid droplets on substrate surfaces commonly are used to measure wettability of liquids on the substrate surface and to evaluate adhesion. The contact angle is defined as the angle between the substrate support surface and the tangent line at the point of contact of the liquid droplet with the substrate. The value of the contact angle of the liquid droplet will depend upon the surface energy of the substrate and the surface tension of the liquid. If perfect or complete wetting takes place between the liquid and the substrate surface by reason of high surface energy, the droplet will spread out over the substrate and the contact angle will approach 0, whereas if wetting is only partial, the resulting contact angle will lie in the range of 0° to 180°. Devices are known for determining the contact angle of the droplet, both by direct measurement of the angle and by indirect calculation based upon measurements of the height, width, and/or radius of the droplet. Most common procedures involve projecting a silhouette image of the deposited droplet onto a screen and determining the contact angle by direct or indirect measurements taken from the silhouette.

Measurements of contact angles commonly are used in industry, both in research as well as in routine testing of surface properties of materials or articles of manufacture. For example, without specific surface treatment, many plastic materials, such as polypropylene and polyethelene, have insufficient wettability for effectively retaining printing inks applied thereto or for bonding decorations or other materials applied to the surface. Contact angle measuring procedures routinely are used in quality control to ensure that proper surface treatment is effected on the material for the required printing, decorating or bonding. Similar procedures are used in numerous other manufacturing or scientific applications. Accurate and repeatable contact angle measurements heretofore have required utilization of flat, horizontal substrate surfaces. In many instances, however, the surfaces of articles of manufacture to be tested are convex, cylindrical, or otherwise curved. In such cases, the liquid droplets of the test liquid tend to slide along the convex or cylindrical surface preventing accurate contact angle measurement.

OBJECTS AND SUMMARY OF THE INVENTION

It is an object of the present invention to provide a method and apparatus for accurately determining the contact angle of liquid droplets applied to convex or otherwise curved substrate surfaces.

Another object is to provide a method and apparatus for applying liquid droplets of a control substance to such convex or otherwise curved substrate surfaces in a manner that permits accurate and repeatable measurement of the contact angle of the deposited droplets.

A further object is to provide a method and apparatus of the foregoing type which is simple and easily repeatable, and hence which lends itself to use in quality control operations of automated production lines.

Other objects and advantages of the invention will become apparent upon reading the following detailed description and upon reference to the drawings, in which:

Figure 1:
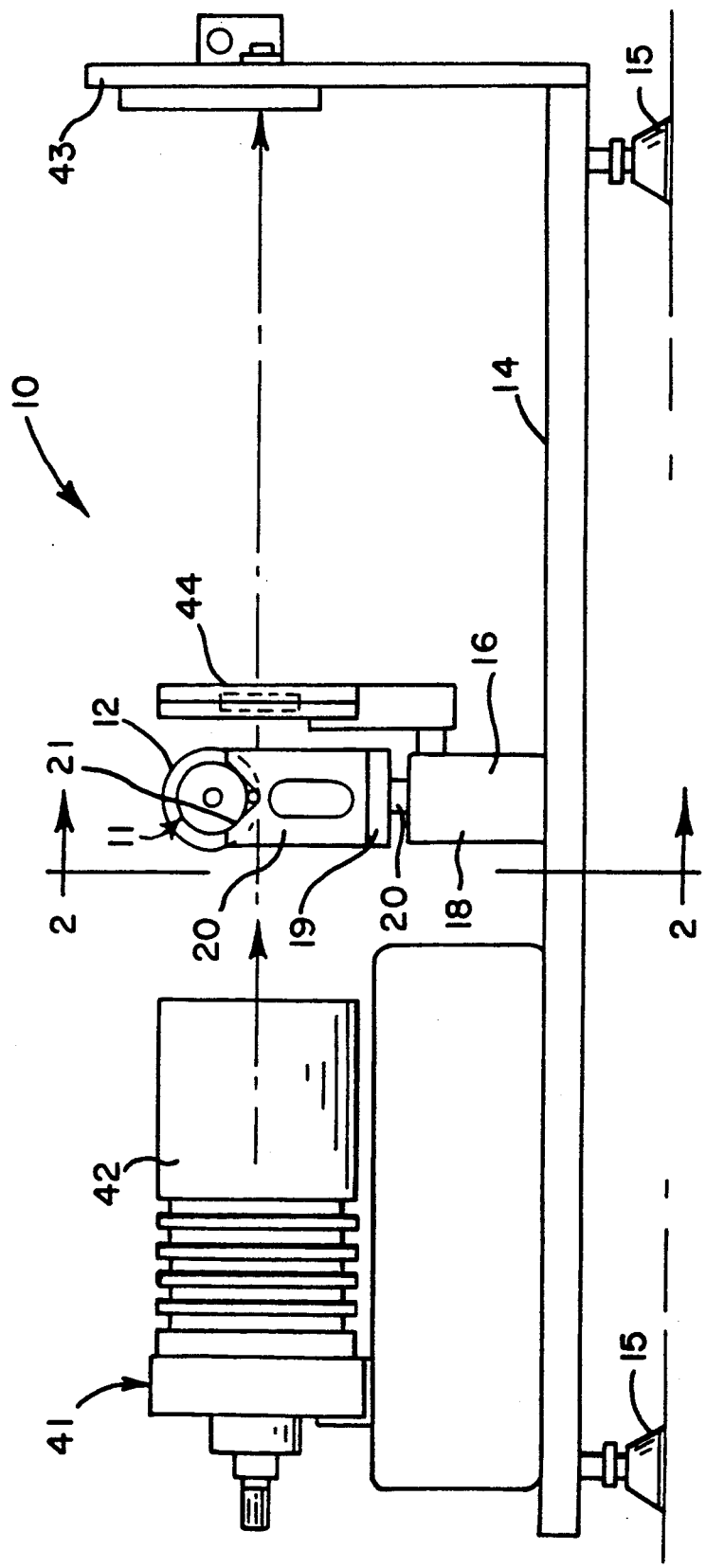
FIG. 1 is a side elevational view of an illustrative apparatus for measuring the contact angles of liquid droplets applied to curved substrate surfaces in accordance with the present invention.

While the invention is susceptible of various modifications and alternative constructions, certain illustrated embodiments thereof have been shown in the drawings and will be described below in detail. It should be understood, however, that there is no intention to limit the invention to the specific forms disclosed, but on the contrary, the intention is to cover all modifications, alternative constructions and equivalents falling within the spirit and scope of the invention.

DESCRIPTION OF THE PREFERRED EMBODIMENTS

Figure 2:
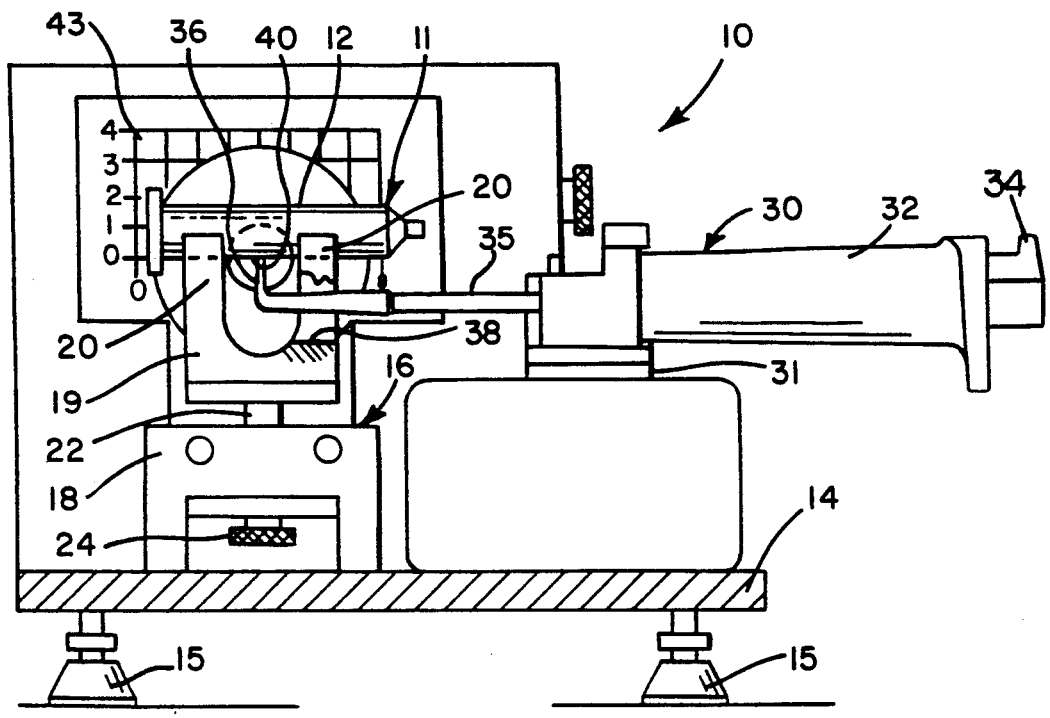
FIG. 2 is an enlarged transverse section of the apparatus shown in FIG. 1, taken in the plane of line 2—2.
Figure 3:
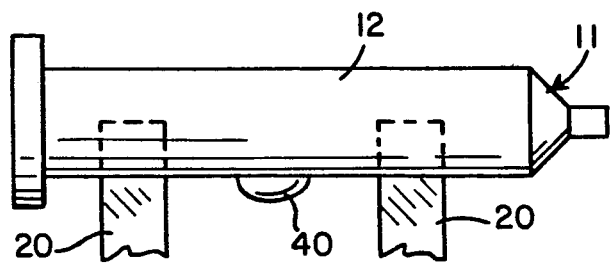
FIG. 3 is an enlarged side view of a test element after a droplet of a test liquid has been applied to a cylindrical surface thereof.

Referring now particularly to the FIGS. 1–3 of the drawings, there is shown an illustrative contact angle measuring apparatus 10 adapted for measuring the contact angle of a liquid droplet of a control substance or test liquid, such as distilled water, applied to convex, cylindrical or other curved surfaces. The apparatus 10 in this instance is shown for use in determining the surface characteristics of a test element 11 in the form of a plastic syringe barrel having an elongated cylindrical body portion 12. The syringe barrel, which may be manufactured of polypropylene or polyethelene, typically will have been surface treated and the contact angle measuring apparatus 10 is utilized for determining the surface characteristics of the cylindrical body portion 11 prior to printing thereon or prior to applying a label, decorative coating, or the like. It will be understood that the apparatus of the present invention may be employed to measure the surface characteristics of various other articles which have cylindrical, convex or other curved surfaces and which are made of plastic, metal or other materials.

The illustrated contact angle measuring apparatus 10 has an elongated horizontal platform 14 supported at opposite ends by adjustable legs 15 for enabling desired leveling of the platform 14. The test element 11 is supported with its cylindrical body portion 12 transversally oriented with respect to the platform 14 by means of a test stand 16. The test stand 16 includes a base 18 mounted on the platform 14 and a vertically positionable, yoke-shaped, test element support 19 having a pair of laterally spaced upstanding legs 20, each formed with an upwardly opening V-shaped slot 21 between which the cylindrical body portion 12 of the test element 11 is horizontally supported. For selectively positioning the test element 11 at a desired elevation on the platform 14, the support 19 has a depending shaft 22 that appropriately cooperates with the shaft of an adjustable knob 24, such as through a threaded coupling, so that rotation of the knob 24 will raise or lower the support 19 relative to the base 18 and platform 14 as desired.

In accordance with the invention, means are provided for depositing a droplet of test liquid onto the underside of the curved substrate surface of the test element and then measuring the contact angle of the deposited droplet while in a suspended state from the underside of the curved surface. To this end, for applying droplets of a test liquid onto the underside of the curved cylindrical surface of the test element 11, a pipette 30 is supported adjacent the test stand 16. The pipette 30 in this case is horizontally supported on a cradle or base 31 transversely to one side of the test stand 16 in aligned relation to the test element 11 carried by the test stand. The pipette 30 is operable in a known manner upon selective actuation of a trigger or plunger 34 for releasing a predetermined, liquid droplet from a discharge end or tube 35.

In carrying out the invention, the discharge tube 35 of the pipette 30 is L-shaped with an upturned end 36 thereof disposed in closely spaced relation to the underside of the cylindrical surface of the test element 11. The illustrated discharge tube 35 of the pipette 30 is positioned through an aperture 38 in one leg 20 of the test stand support 19 so that the upturned end 36 is located centrally between the support legs 20 directly under the lowermost point of the cylindrical surface. The pipette 30 is operable for discharging relatively small sized liquid droplets wherein the liquid droplets are of a smaller radius than the radius of curvature of the downwardly facing curved (cylindrical) surface, such as on the order of 10 microliters, and is positioned with a small clearance, such as 1-2 millimeters, between the discharge end 36 of the pipette and the underside of the curved substrate surface to be tested so that as the test liquid is released from the upturned end 36 it will engage and adhere to the underside of the curved substrate surface. The pipette preferably is supported on the cradle or base 31 for limited pivotal or rocking movement such that upon release of the test liquid into adhering engagement with the underside of the curved substrate surface the outwardly extending end of the pipette may be lifted slightly, causing the upturned discharge end 36 to be lowered leaving the test liquid suspended from the underside of the curved substrate surface in the form of a droplet 40. It has been found that gravity will cause the deposited droplet 40 to suspend from a lowermost portion of the cylindrical surface even if slightly misdirected onto the surface, but because of the relatively small size of the droplet, the droplet 40 otherwise is substantially unaffected by gravity.

For measuring the contact angle of the liquid droplet 40 suspended from the underside of the curved cylindrical surface of the test element 11, a light-projection contact angle measuring device 41 is provided on the platform 14. The light projection measuring device 41 includes a light beam generating lamp 42, a magnifying lens 44 and an image projection screen 43, all which may be of a conventional type, such as sold by Tantec, Inc., assignee of the present application. The lamp 42 is disposed at one end of the platform 14 and is adapted for projecting a substantially horizontal light beam across the suspended droplet 40 and through the magnifying lens 44 disposed on the opposite side of the droplet 40, such that a magnified silhouette image of the droplet is projected onto the screen 43 at the end of the platform 14 opposite the lamp 42. The contact angle may be accurately determined from the silhouette image, by indirect or direct measurement, as known in the art.

It will be appreciated that once the test stand support 19 has been adjusted for the particular configured test element or article to be tested, the apparatus 10 is adapted for quick, accurate, and repeatable contact angle measurements of liquid droplets or such similar articles. The articles may easily be positioned onto the support legs 20 of the test stand, without further adjustment of the test stand support 19 and without cumbersome fastening or securing means. Indeed, positioning and removal of successive test elements 11 onto the test stand 16 may be automatically effected as part of an automated production line, or as part of an automatic and continuous quality control line. Moreover, even if the liquid droplet is not deposited exactly onto the lowermost point of the cylindrical or convex surface of the test element, it will migrate under the influence of gravity to the lowermost point from which it will be suspended for accurate, repeated contact angle measurement.

Figure 4B:
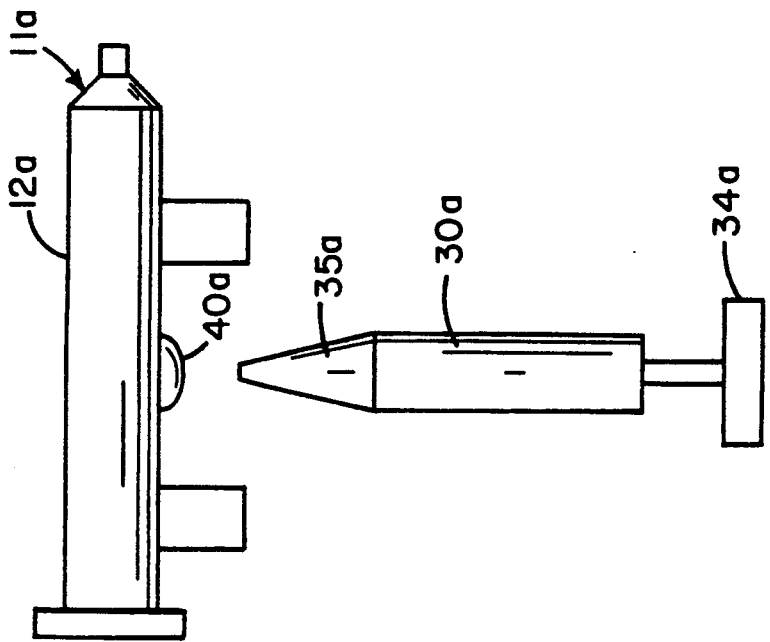
FIGS. 4A and 4B are partially diagrammatic illustrations illustrating an alternative method and apparatus according to the present invention for applying liquid droplets of a test liquid onto a curved substrate surface of a test element.
Figure 4A:
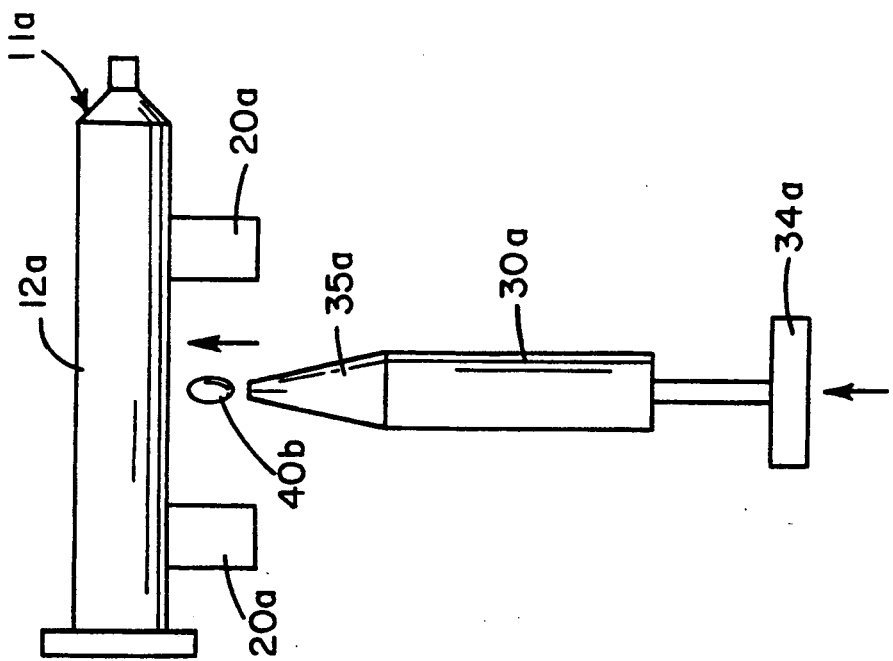

Referring now to FIGS. 4A and 4B, there is shown an alternative means and method for applying liquid droplets to the underside of a curved substrate surface of a test element, wherein items similar to those described above have been given similar reference numerals with the distinguishing suffix "a". In this embodiment, a pipette 30a is vertically disposed immediately below the lowermost point of the cylindrical substrate surface of the test element 11a between the support legs 20a of the test stand with the discharge end 35a of the pipette 30b located a predetermined, discrete distance, such as 3-4 millimeters, from the underside of the substrate surface (FIG. 4A). Actuation of the plunger or trigger 34a of the pipette 30a in this case causes a predetermined relatively small quantity of test liquid to be squirted upwardly out of the pipette into contact with the underside of the substrate surface, attaching to it in the form of the droplet 40a (FIG. 4B). As in the previous embodiment, the droplet 40a will find the lowest point on the curved surface and be suspended therefrom, without substantial further effect by gravity, for accurate and repeatable contact angle measurement. It will be understood that, in lieu of the vertically oriented pipette 30a, the test liquid could be squirted onto the underside of the curved substrate surface from a pipette similar to that disclosed in the embodiment of FIGS. 1-3, but with the upturned discharge end thereof located a greater distance from the curved surface.

Figure 5A:
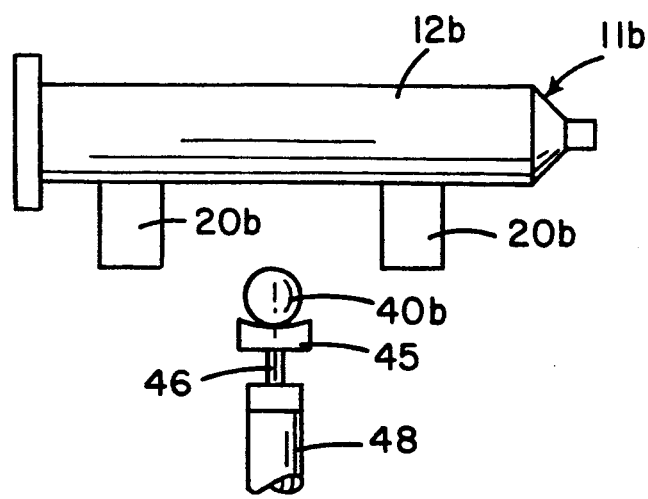
FIGS. 5A–5C are partially diagrammatic illustrations of a further alternative method and apparatus for applying liquid droplets of a test liquid onto a curved substrate surface of a test element.
Figure 5B:
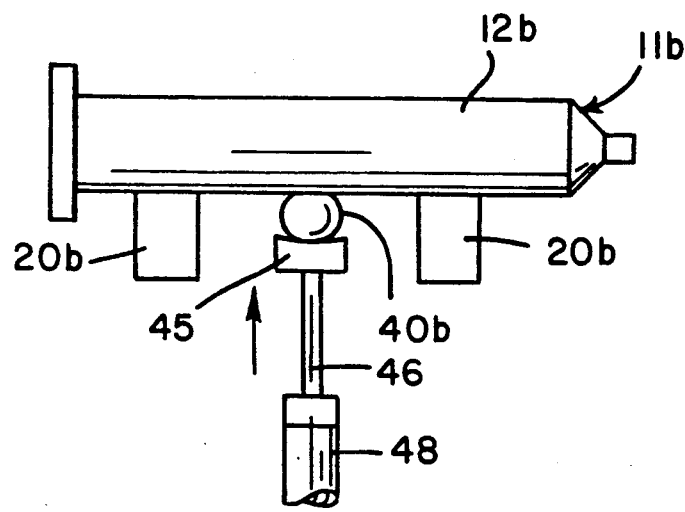
Figure 5C:
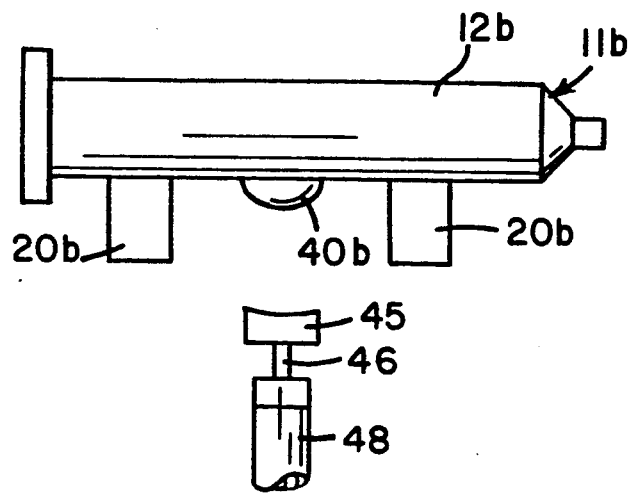

Referring now to FIGS. 5A-5C, there is shown still a further alternative means and method for depositing liquid droplets onto the underside of a curved substrate surface of a test element, wherein items similar to that described above have been given similar references numerals with the distinguishing suffix "b" added. In this embodiment, a vertically moveable droplet transfer plate 45 is disposed below the test element 11b between the legs 20b of the test stand. The liquid droplet transfer plate 45 in this case is mounted at the end of a piston rod 46 of a vertically oriented pneumatic or hydraulic cylinder 48. The surface of the plate 45 is made of a material with relatively low surface energy, such as graphite, so that a droplet 40b of a test liquid deposited thereon will remain in nearly spherical form with a substantial contact angle. The plate 45 is moveable upon appropriate actuation of the cylinder 48 between a lowered position, at which location a predetermined amount of test liquid may be deposited onto the plate, such as by manual or automatic actuation of a conventional pipette, and a raised position at which location the top side of the droplet 40b will engage the underside of the curved substrate surface and because of the relatively low surface energy of the plate 45, will readily transfer onto the substrate surface and be retained thereon upon lowering of the plate 45. The droplet transfer plate 45 preferably is formed with a slightly concave upper surface for facilitating retention of the droplet 40b during raising movement into contact with the test element 11b. Upon retraction of the droplet transfer plate 45 following depositing of the droplet 40b onto the underside of the test element 11b, the droplet 40b remains in a suspended state on the underside curved substrate surface, in the manner previously described, for reliable contact angle determination.

From the foregoing, it can be seen that the apparatus and method of the invention are adapted for rapid, accurate, and repeatable determination of the contact angles of liquid droplets applied to convex, cylindrical, or otherwise curved substrate surfaces. The droplets of the test liquid are deposited onto the curved substrate surface in a manner that enables reliable determination of the contact angles, and the simplicity of the method and apparatus permit its use in automated production and quality control operations.

What is claimed is:

1. An apparatus for determining the contact angle of a droplet of test liquid on a curved substrate surface of an article comprising means for supporting the article with the curved substrate surface thereof facing downwardly, means for transferring onto the downwardly facing curved surface a droplet of test liquid of smaller radius than the radius of curvature of the downwardly facing curved surface so that the droplet is suspended from said surface, and means for determining the contact angle of the transferred droplet while suspended from the downwardly facing curved surface.

2. The apparatus of claim 1 in which said contact angle determining means includes a screen, and means for directing a light beam across the suspended droplet such that an image thereof is projected onto said screen from which the contact angle is measurable.

3. The apparatus of claim 1 in which said droplet transferring means includes a selectively actuatable pipette having a discharge end disposed below the downwardly facing curved substrate surface for directing the droplet of test liquid upwardly against the force of gravity onto the underside of the downwardly facing curved surface.

4. The apparatus of claim 3 in which said pipette discharge end is disposed in relatively closely spaced relation to said downwardly facing substrate surface, and said pipette is operable upon actuation for releasing a predetermined relatively small quantity of said test liquid from the discharge end thereof into contacting relation with said curved surface with the released liquid being suspendable from the curved surface as a droplet in separated relation to said pipette discharge end.

5. The apparatus of claim 4 in which said pipette is movable for lowering the discharge end thereof upon release of test liquid into contacting relation with said curved surface.

6. The apparatus of claim 3 including means for supporting said pipette in outwardly extended relation from one side of said article, and said pipette discharge end is in the form of a discharge tube having an upturned end in closely adjacent relation to the underside of said downwardly facing curved surface.

7. The apparatus of claim 6 in which said pipette supporting means supports said pipette for limited pivotal movement so that upon release of said test liquid into contacting relation with said curved surface the pipette may be pivoted to lower the discharge end thereof a greater distance from the curved surface.

8. The apparatus of claim 4 in which said contact angle determining means includes a screen, and means for directing a light beam across the suspended droplet such that an image thereof is projected onto said screen from which the contact angle is measurable.

9. The apparatus of claim 3 in which the discharge end of said pipette is located a discreet distance below said downwardly facing curved surface, and said pipette is operable upon actuation for squirting a droplet of said test liquid out of said discharge end upwardly into contact with said downwardly facing curved substrate surface for suspension from said curved surface.

10. The apparatus of claim 3 in which said article supporting means includes a support having a pair of upstanding legs upon which an article may be supported with the curved substrate surface thereof located in a downwardly facing direction between said legs.

11. The apparatus of claim 10 in which the discharge end of said pipette is disposed between said support legs.

12. The apparatus of claim 11 including a platform upon which said article supporting means and contact angle determining means are disposed, and said article support means is adjustable positionable for supporting the article at a desired position with respect to said support stand and contact angle determining means.

13. The apparatus for determining the contact angle of a droplet of test liquid on a cylindrical substrate surface of an article comprising means for supporting the article with a portion of the cylindrical substrate surface thereof facing downwardly, means for transferring onto the downwardly facing portion of said cylindrical substrate surface a droplet of test liquid of smaller radius than the radius of curvature of the downwardly facing cylindrical surface so that the droplet is suspended from said surface, and means for determining the contact angle of the transferred droplet while suspended from the downwardly facing portion of the cylindrical substrate surface.

14. The apparatus of claim 13 in which said droplet transferring means includes a selectively actuatable pipette having a discharge end disposed below said downwardly facing portion of said cylindrical substrate surface for directing the droplet of test liquid upwardly against the force of gravity onto the underside of the downwardly facing, curved surface, and said contact angle determining means includes a screen, and means for directing a light beam across the suspended droplet such that an image thereof is projected onto said screen from which the contact angle is measurable.

15. An apparatus for determining the contact angle of said droplet of test liquid on a convex substrate surface of an article comprising means for supporting the article with the convex substrate surface thereof facing downwardly, means for transferring onto the downwardly facing convex surface a droplet of test liquid of smaller radius than the radius of curvature of the downwardly facing convex surface so that the droplet is suspended from said surface, and means for determining the contact angle of the deposited droplet while suspended from the downwardly facing convex surface, contact angle determining means including a screen, and means for directing a light beam across the suspended droplet such that an image thereof is projected onto said screen from which the contact angle is measurable.

16. The apparatus of claim 15 in which said droplet transferring means includes a selectively actuatable pipette having a discharge end disposed below the downwardly facing curved substrate surface for directing the droplet upwardly against the force of gravity onto the underside of the downwardly facing surface.

17. A method of determining the contact angle of a droplet of test liquid on a curved substrate surface of an article comprising the steps of:

supporting the article with the curved surface thereof facing downwardly, transferring onto said downwardly facing curved surface a droplet of test liquid of smaller radius than the radius curvature of the downwardly facing curved surface so that the droplet is suspended from said surface, and determining the contact angle of the transferred droplet while suspended from the downwardly facing curved surface.

18. The method of claim 17 including determining the contact angle by directing a light beam across the suspended droplet and projecting an image thereof on a screen, and measuring the contact angle based upon the projected image.

19. The method of claim 18 including projecting a magnified silhouette image of the suspended droplet onto the screen, and measuring the contact angle based upon the magnified silhouette image.

20. The method of claim 17 including transferring said droplet of test liquid by releasing a predetermined quantity thereof upwardly against the force of gravity onto said downwardly facing curved surface.

21. The method of claim 17 including transferring said droplet of test liquid by squirting a predetermined quantity thereof upwardly into contact with said downwardly facing curved surface.

22. A method of determining the contact angle of a droplet of test liquid on a curved substrate surface of an article comprising the steps of:

supporting the article with the curved surface thereof facing downwardly, transferring onto said downwardly facing curved surface a droplet of test liquid of smaller radius than the radius of curvature of the downwardly facing curved surface so that the droplet is suspended from said surface, allowing said droplet to migrate to and suspend from a lowermost point on said downwardly facing curved surface under the force of gravity, and determining the contact angle of said droplet while suspended from said downwardly facing curved surface by directing a light beam across the suspended droplet and projecting an image thereof on a screen from which said contact angle is measurable.

23. An apparatus for determining the contact angle of a droplet of test liquid on a curved substrate surface of an article comprising means for supporting the article with the curved substrate surface thereof facing downwardly, means for transferring a droplet of test liquid onto the downwardly facing curved surface so that droplet is suspended therefrom, said droplet transferring means including a selectively actuatable pipette having a discharge end located a discreet distance below said downwardly facing curved substrate surface, said pipette being operable upon actuation for squirting a droplet of said test liquid out of said discharge end upwardly into contact with said downwardly facing curved substrate surface for suspension from said curved surface, and means for determining the contact angle of the transferred droplet while suspended from the downwardly facing curved surface, said contact angle determining means including a screen and means for directing a light beam across the suspended droplet such that an image thereof is projected on said screen from which the contact angle is measurable.

24. An apparatus for determining the contact angle of a droplet of test liquid on a curved substrate surface of an article comprising means for supporting the article with the curved substrate surface thereof facing downwardly, means for transferring a droplet of test liquid into the downwardly facing curved surface so that droplet is suspended therefrom, said droplet transferring means including a droplet transfer plate disposed below said downwardly facing curved substrate surface, and means for moving said plate between a retracted position where a predetermined sized droplet of test liquid may be deposited onto said plate and a raised position for depositing said droplet onto said downwardly facing curved surface, and means for determining the contact angle of the transferred droplet while suspended from the downwardly facing curved surface.

25. The apparatus of claim 24 in which said plate moving means includes a hydraulic cylinder having an extendable and retractable cylinder rod, said plate being mounted at the end of said cylinder rod.

26. The apparatus of claim 24 in which said liquid droplet transfer plate has a droplet support surface formed of a material having a low surface energy such that a droplet of test liquid deposited thereon remains in substantial spherical form.

27. The apparatus of claim 26 in which said liquid droplet support surface of said plate has a concave configuration.

28. The apparatus of claim 24 in which said contact angle determining means includes a screen, and means for directing a light beam across the suspended droplet such that an image thereof is projected on said screen from which the contact angle is measurable.

29. A method of determining the contact angle of a droplet of test liquid on a curved substrate surface of an article comprising the steps of:

supporting the article with the curved surface thereof facing downwardly, transferring a droplet of test liquid onto said downwardly facing curved surface by depositing a droplet of said test liquid onto a droplet transfer plate disposed below said downwardly facing curved surface and elevating said plate to a point that said droplet is brought into adhering engagement with said downwardly facing curved surface such that upon lowering of said plate the droplet remains in a suspended state on said curved substrate surface, and determining the contact angle of the transferred droplet while suspended from the downwardly facing curved surface.

* * * * *